US008163970B2

(12) United States Patent
Takegami et al.

(10) Patent No.: US 8,163,970 B2
(45) Date of Patent: **\*Apr. 24, 2012**

(54) METHOD FOR ADIABATIC COOLING TYPE CRYSTALLIZATION OF ORGANIC COMPOUND AND APPARATUS THEREFOR

(75) Inventors: Keizo Takegami, Chuo-ku (JP); Junji Wakayama, Chuo-ku (JP); Kiwamu Ishii, Chuo-ku (JP); Kenji Ouchi, Chuo-ku (JP)

(73) Assignee: Tsukishima Kikai Co., Ltd., Tokyo (JP)

( * ) Notice: Subject to any disclaimer, the term of this patent is extended or adjusted under 35 U.S.C. 154(b) by 737 days.

This patent is subject to a terminal disclaimer.

(21) Appl. No.: 11/887,293

(22) PCT Filed: Mar. 7, 2006

(86) PCT No.: PCT/JP2006/304330
§ 371 (c)(1),
(2), (4) Date: Sep. 27, 2007

(87) PCT Pub. No.: WO2006/112186
PCT Pub. Date: Oct. 26, 2006

(65) Prior Publication Data
US 2009/0112040 A1    Apr. 30, 2009

(30) Foreign Application Priority Data
Mar. 30, 2005    (JP) ................................. 2005-100173

(51) Int. Cl.
*C07C 7/14* (2006.01)
(52) U.S. Cl. ......... 585/815; 585/812; 585/816; 585/817
(58) Field of Classification Search .................. None
See application file for complete search history.

(56) References Cited

U.S. PATENT DOCUMENTS

| 3,592,016 | A | | 7/1971 | Bligh |
| 3,992,900 | A | | 11/1976 | Campbell |
| 4,743,434 | A | | 5/1988 | Thijssen et al. |
| 5,329,061 | A | * | 7/1994 | Swift ............................ 585/805 |

FOREIGN PATENT DOCUMENTS

| DE | 972651 | 8/1959 |
| DE | 102 42 746 | 3/2004 |
| EP | 0 646 399 | 4/1995 |
| JP | 53-033551 | 9/1978 |
| JP | S56-131528 | 10/1981 |
| JP | 3-042001 | 2/1991 |
| JP | 4-327542 | 11/1992 |
| JP | 7-082210 | 3/1995 |
| JP | 2003-265150 | 9/2003 |

* cited by examiner

*Primary Examiner* — Tam M Nguyen
(74) *Attorney, Agent, or Firm* — DLA Piper LLP (US)

(57) ABSTRACT

A method including carrying out adiabatic cooling and evaporation operation of a coolant in a crystallizer (20) for a mixture solution of a target organic compound containing the coolant; taking out crystal slurry produced by the operation from the crystallizer (20); pressurizing evaporated vapor to a pressure higher than the operation pressure in the crystallizer (20) by a compressor (30) and then introducing the vapor to an absorption condenser (10); cooling for condensation the mixture solution of organic compound and the evaporated vapor that has been pressurized while allowing them to contact each other in the absorption condenser (10); introducing the crystal slurry taken out of the crystallizer (20) to a purification means (70) for purification of the crystal; and introducing a clarified liquid in the purification means (70) to at least one of the crystallizer (20) and the absorption condenser (10).

7 Claims, 3 Drawing Sheets

METHOD FOR ADIABATIC COOLING TYPE CRYSTALLIZATION OF ORGANIC COMPOUND AND APPARATUS THEREFOR

BACKGROUND OF THE INVENTION

1. Field of the Invention

The present invention relates to a method for adiabatic cooling type crystallization of organic compound and an apparatus therefore, and more particularly to a method and an apparatus suitable for obtaining paraxylene crystal.

2. Description of the Related Art

Separation and purification of a certain kind of isomer mixture are difficult in distillation operation because boiling points of components constituting the mixture are close to each other. However, there are many cases where melting points are largely different depending on the difference in molecular structures, and therefore, separation by crystallization operation is often effective.

There are methods of extraction crystallization and addition compound crystallization in which a solvent-agent (extractant, additive) is added to a two-component eutectic system or a multi-component eutectic system as a third component; however, these are disadvantageous to recover the solvent-agent.

In this regard, a method in which a liquified gas component is used as a coolant is advantageous because its recovery is easy.

The present inventors have found that it is effective to carry out crystallization operation, with the use of propane (propene, ethylene, carbonic acid gas, ammonia, or the like) as a direct injecting coolant, for a multi-component eutectic system such as xylene mixture (m-xylene+o-xylene+ethylbenzene+p-xylene system) that is a raw material for a typical. p-xylene production in a petrochemical industrial process or a xylene mixture (m-xylene+o-xylene+p-xylene system) after isomerization reaction.

In this case, it is possible to carry out the crystallization operation in a jacket type crystallizer; however the crystallization is necessary to be carried out by cooling p-xylene in the multi-component eutectic system to about −30 degrees C. to −60 degrees C. Therefore, it is required to provide the crystallizer with a cooling surface scraper mechanics and a refrigeration unit by which the evaporated coolant from the jacket is compressed by a compressor, for example, under a high pressure of 20 atmospheres, followed by allowing this to be liquefied and circulated to the jacket.

Using such a crystallizer results in not only an increase in power cost of the compressor but also increases in facility cost and maintenance cost because the crystallizer has to be provided with a cooling surface scraper mechanics that requires complex and frequent maintenance.

On the other hand, another system in which a heat pump is used is conceivable (Patent document 1: Japanese Patent Application Laid-Open Publication No. 1992-327542 ), but the system is not necessarily suitable in view of facility cost to construct the heat pump.

SUMMARY OF THE INVENTION

Main objects of the present invention are to provide a method for adiabatic cooling type crystallization of organic compound and an apparatus therefore in which running cost (including maintenance cost) and facility cost can be reduced.

Other objects of the present invention are to provide a method. and an apparatus suitable for crystallization of p-xylene.

The present invention to solve the above problems is carried out as follows.

<Aspect According to claim 1>

A method for adiabatic cooling type crystallization of organic compound comprising:

carrying out adiabatic cooling, as for crystallization operation of target organic compound and evaporation operation of a coolant which is directly introduced in a crystallizer for a mixture solution of a target organic compound containing the coolant;

taking out crystal slurry produced by the operation from the crystallizer;

pressurizing evaporated vapor to a pressure higher than the operation pressure in the crystallizer by a compressor and then introducing the pressurized coolant vapor to an absorption condenser, removing the heat of absorption and condensation, cooling the mixture solution of organic compound and the evaporated coolant vapor that has been pressurized, while allowing them to contact each other in the absorption condenser; and introducing the crystal slurry taken out of the crystallizer to a purification means to purify the crystal, and introducing a clarified liquid in the purification means to at least one of the crystallizer and the absorption condenser.

(Advantageous Effect)

When the adiabatic cooling and the evaporation operation of the coolant are carried out for the mixture solution of the target organic compound containing the coolant in the crystallizer, heat of crystallization is taken away in association with evaporation of substantially only the liquid coolant component, and crystal is crystallized. The evaporated vapor is pressurized to a pressure higher than the operation pressure in the crystallizer by the compressor, and then introduced to the absorption condenser for condensation. The reason why the evaporated vapor is pressurized to a pressure higher than the operation pressure in the crystallizer by the compressor is that the vapor is pressurized by the compressor in order to secure a temperature difference for the condensation. In the absorption condenser, since the evaporated vapor is brought into contact with the mixture solution of organic compound having a lower vapor pressure, the boiling point rises, thereby raising the temperature at which absorption and condensation can take place. Accordingly, a smaller degree of pressurization suffices the need, and a smaller energy input from outside suffices the need for the condensation.

Continuous crystallization operation can be carried out by introducing condensate liquid from the absorption condenser to the crystallizer. Taking crystallization of p-xylene as an example, propane is used as a coolant, the pressure in the crystallizer is, for example, normal atmospheric pressure, and the pressure in the absorption condenser is, for example, about eight atmospheric pressure by means of pressurization by the compressor.

According to the above operation, crystallization operation is possible without constructing the crystallizer as a pressure resistant container. When at least a compressor and an absorption condenser are included as other necessary apparatuses, crystallization operation can be carried out, and therefore, an expensive structure installed with a refrigeration unit that was used in the prior art is not necessary, thus giving rise to an economical apparatus in view of entire system cost and running cost.

The crystal slurry produced in the crystallizer is taken out and purified by the purification means to enhance the purity for making a product. Since the target component remains in the clarified liquid in the purification means, the clarified liquid can be introduced to at least one of the crystallizer and the absorption condenser. Accordingly, the recovery rate of the crystal of the target component can be enhanced. When the clarified liquid is sent back to the crystallizer, an absorption amount of the coolant (gas) is increased, thereby allowing the cooling heat in the crystallizer to have an allowance.
<Aspect According to claim 2>
The method for adiabatic cooling type crystallization of organic compound according to claim 1, where the crystal slurry taken out of the crystallizer is introduced to the purification means after it is concentrated by a concentration means.
(Advantageous Effect)
The crystal slurry taken out of the crystallizer is introduced to the purification means after it is concentrated by the concentration means such as a centrifuge, a filter, or a liquid cyclone preferable in terms of apparatus cost. Thus, not only can crystal having high purity be obtained by the purification means but also the purification efficiency in the purification means is enhanced because the mother liquid is separated in advance.
<Aspect According to claim 3>
The method for adiabatic cooling type crystallization of organic compound according to claim 1, where the clarified liquid in the clarified portion in the crystallizer is introduced to the absorption condenser.
(Advantageous Effect)
By sending back the clarified liquid in the clarified portion (upper portion) in the crystallizer to the absorption condenser, condensation of the coolant vapor can be carried out at a further lower pressure. In this case, it is preferred that the clarified liquid is allowed to combine with the original liquid and supplied to the absorption condenser for absorption and condensation in a condition of a lowered concentration of the coolant.
<Aspect According to claim 4>
The method for adiabatic cooling type crystallization of organic compound according to claim 1, where the purification means is an vertical melt purification column having a clarified liquid discharge means in the upper portion and a heating means in the lower portion, to which the crystal slurry taken out of the crystallizer is introduced, in the purification column, the crystal moving to the lower portion is molten by the heating means in the lower portion, part of the molten matter or the molten liquid containing the crystal is taken out for making a product, the other portion is allowed to rise, as a reflux liquid, through the crystal group that is falling, the mother liquid is washed out with this reflux liquid, the purified crystal is allowed to precipitate downward, and the clarified liquid that has reached the clarified liquid discharge means in the upper portion is introduced to at least one of the crystallizer and the absorption condenser.
(Advantageous Effect)
As to the crystal slurry taken out of the crystallizer, when a product with higher purity is obtained, purification with the use of the purification means is preferred. With the use of the vertical melt purification means according to claim 4, crystal with high purity can be obtained by countercurrent contact of the crystal moving to the lower portion with the liquid rising as a reflux liquid.
<Aspect According to claim 5>
The method for adiabatic cooling type crystallization of organic compound according to claim 1, where the purification means is an vertical melt purification column having a clarified liquid discharge means in the lower portion and a heating means in the upper portion, to which the crystal slurry taken out of the crystallizer is introduced, in the purification column, the crystal moving to the upper portion is molten by the heating means in the upper portion, part of the molten matter or the molten liquid containing the crystal is taken out for making a product, the other portion is allowed to fall, as a reflux liquid, through the crystal group that is rising, the mother liquid is washed out with this reflux liquid, the purified crystal is allowed to move upward, and the clarified liquid that has reached the clarified liquid discharge means in the lower portion is introduced to at least one of the crystallizer and the absorption condenser.
(Advantageous Effect)
The vertical melt purification column according to claim 5 has a structure in which the upper portion and the lower portion are in reverse to those in the structure according to claim 4, and purification can also be carried out by this vertical melt purification column.
<Aspect According to claim 6>
The method for adiabatic cooling type crystallization of organic compound according to claim 1, where the operation pressure in the crystallizer is vacuum or equal to or lower than four atmospheric pressure.
(Advantageous Effect)
As to the operation pressure (evaporation pressure) in the crystallizer, the operation is preferably carried out at around normal atmospheric pressure and at most at four atmospheric pressure when a pressure resistance property required for the crystallizer and the like, the separation method of produced crystal, and the apparatus are taken into consideration.
<Aspect According to claim 7>
The method for adiabatic cooling type crystallization of organic compound according to claim 1, where the concentration of the coolant in the absorption condensate introduced from the absorption condenser to the crystallizer is set to from 1 to 70%.
(Advantageous Effect)
When the concentration of the coolant in the absorption condensate becomes higher, the crystallization point becomes lower, and the vapor pressure also becomes lower. When the concentration of the coolant in the absorption condensate becomes lower, the vapor pressure becomes lower in relation to the partial pressure. Accordingly, the highest point of the vapor pressure exists. When the concentration of the coolant in the absorption condensate is from 1 to 70%, the operation around the highest point of the vapor pressure is possible.
<Aspect According to claim 8>
The method for adiabatic cooling type crystallization of organic compound according to claim 1, where the mixture solution of organic compound is a xylene mixture containing paraxylene, from which paraxylene crystal is obtained.
(Advantageous Effect) The method is advantageous to obtain paraxylene crystal.
<Aspect According to claim 9>
The method for adiabatic cooling type crystallization of organic compound according to claim 1, where the mixture solution of organic compound is a hexane mixture containing cyclohexane, from which cyclohexane crystal is obtained.
(Advantageous Effect)
The method is advantageous to obtain cyclohexane crystal.
<Aspect According to claim 10>
An apparatus for adiabatic cooling type crystallization of organic compound comprising:
a crystallizer in which adiabatic evaporation operation of a coolant is carried out for a mixture solution of a target organic compound containing the coolant;
a means to take out crystal slurry produced by this operation from the crystallizer;

a compressor that pressurizes evaporated vapor in the crystallizer to a pressure higher than the operation pressure in the crystallizer and introduces the vapor to an absorption condenser;

the absorption condenser that carries out condensation while bringing the mixture solution of organic compound into contact with the evaporated vapor that has been pressurized;

a means to introduce this absorption condensate to the crystallizer;

a purification means to carry out crystal purification of the crystal slurry taken out of the crystallizer; and a means to introduce a clarified liquid in the purification means to at least one of the crystallizer and the absorption condenser.

(Advantageous Effect)

The apparatus offers an advantageous effect similar to that of the aspect according to claim 1.

To summarize the effects described in the above sections of advantageous effect, cooling (crystallization) is possible in the facility for cooling crystallization without installing an unavoidable apparatus to scrape crystal that is crystallized on the cooling surface, and a necessary amount of energy consumed for the cooling can be reduced, thereby making it possible to reduce the running cost and facility cost. Further, the method and the apparatus are suitable for crystallization of p-xylene. Furthermore, since purification is carried out by the purification means, the purity of the crystal can be enhanced. Still further, since the target component remains in the clarified liquid in the purification means, the crystallization efficiency becomes higher by introducing the clarified liquid to at least one of the crystallizer and the absorption condenser.

DETAILED DESCRIPTION

Hereinafter, exemplary embodiments of the present invention will be explained in detail.

<First Embodiment>

Figure 2:
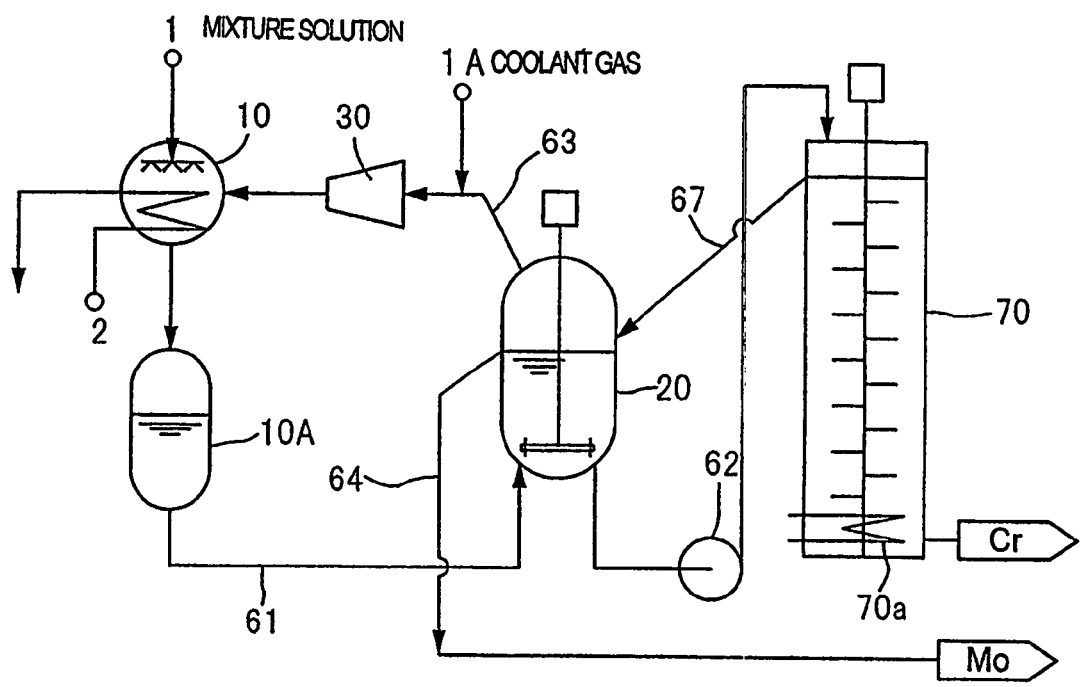
FIG. 2 is a flow sheet of a first embodiment.

FIG. 2 represents a first embodiment, which includes an absorption condenser 10, a crystallizer 20, a compressor 30, and a solid-liquid separation means to take out crystal portion.

A mixture solution 1 of a target organic compound containing a coolant (target liquid for crystallization operation, for example, a liquid of multi-component eutectic mixture containing p-xylene and its isomer) is introduced to the absorption condenser 10 and allowed to absorb coolant vapor (for example, propane) here to be condensed, making a homogeneous liquid mixed with the coolant. The liquid is introduced to the crystallizer 20 via a piping path 61 from a temporary storage tank 10A for absorption condensate, and adiabatic cooling and evaporation operation of the coolant are carried out for the condensed liquid containing the coolant in the crystallizer 20.

Figure 3:
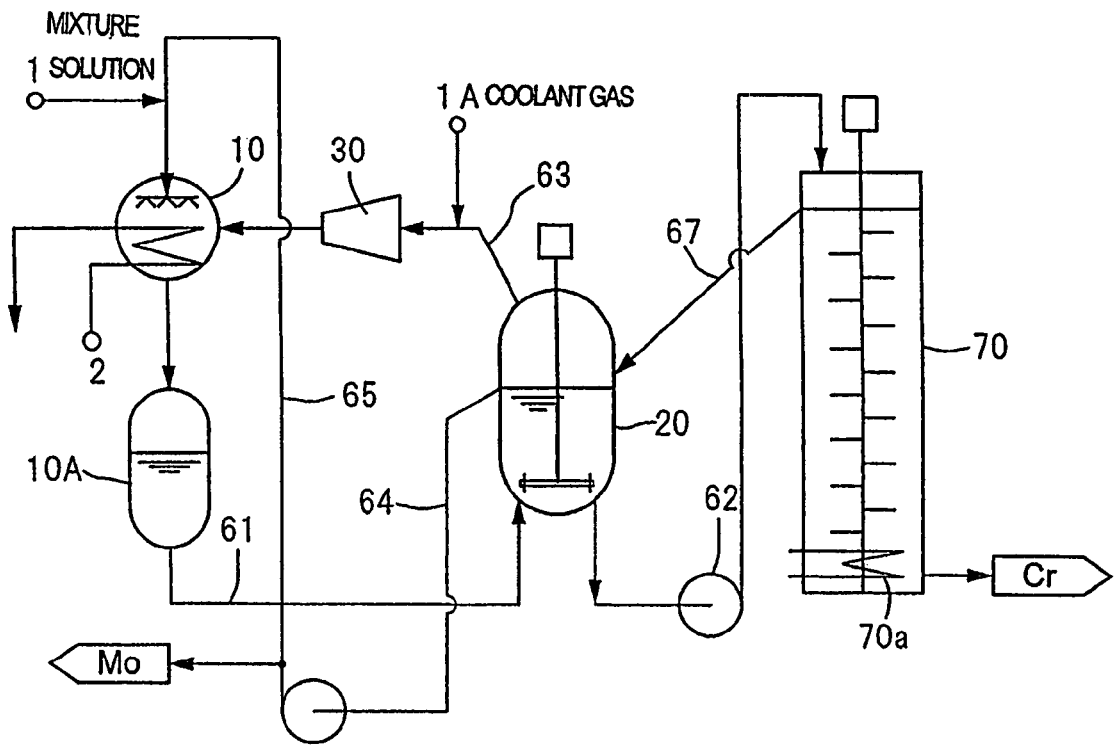
FIG. 3 is a flow sheet of a second embodiment.
Figure 4:
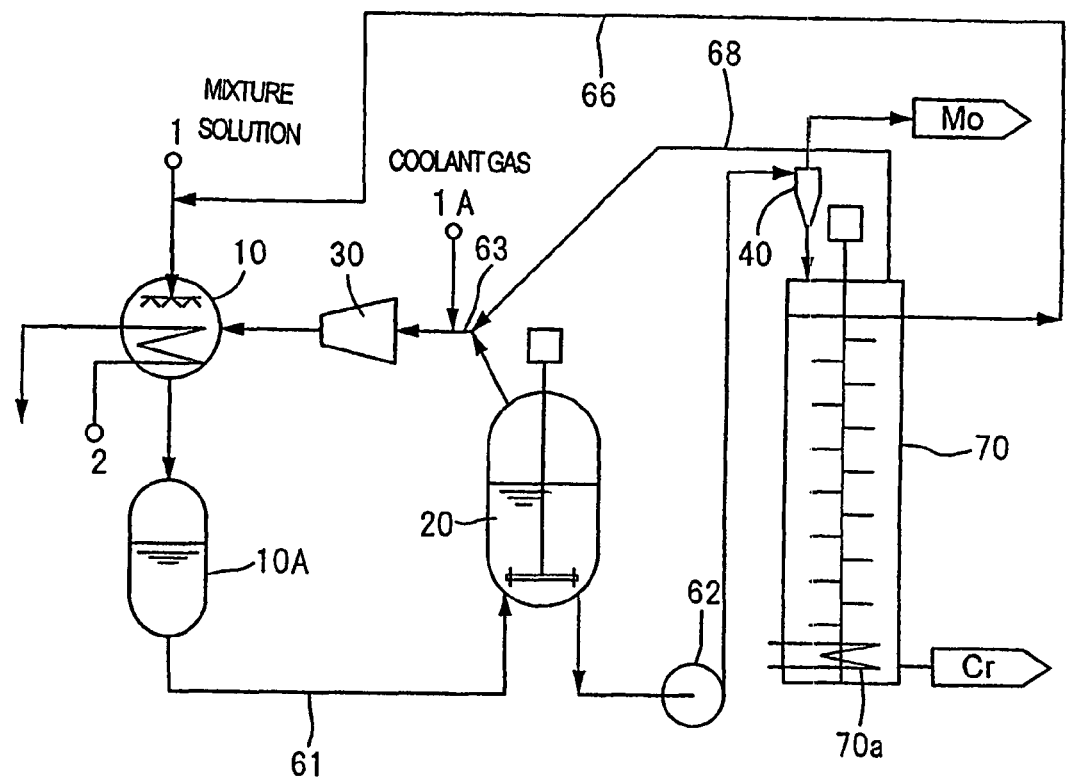
FIG. 4 is a flow sheet of a third embodiment.

Crystal slurry produced by this operation is taken out of the crystallizer 20 by a pump 62 and is preferred to be purified with the use of a purification means in order to obtain a product with higher purity. Examples in FIGS. 2 to 4 are examples that the crystal slurry taken out of the crystallizer 20 is introduced to an vertical melt purification column 70 having a clarified liquid discharge means in the upper portion and a heating means 70a in the lower portion. The vertical melt. purification column 70 constitutes a solid-liquid separation means to take out crystal portion.

In the purification column 70, crystal moving to the lower portion is molten by the heating means 70a in the lower portion, part of the molten matter or the molten liquid containing the crystal is taken out for making a product, the other portion is allowed to rise, as a reflux liquid, through the crystal group that is falling, the mother liquid is washed out with this reflux liquid, the purified crystal is allowed to precipitate downward, the mixed mother liquid of the reflux liquid that has reached the clarified liquid discharge means in the upper portion and the mother liquid is discharged to be sent back to the crystallizer 20 in the previous stage via a piping path 67. Crystal Cr is taken out of the lower portion.

It is well known that purification can be carried out by this kind of countercurrent contact of crystal moving to the lower portion with the mother liquid rising as a reflux liquid (for example, Japanese Patent Application Laid-Open Publication No. 1994-91103), and therefore the detail is not described here. Note that the purification means of the present invention includes a mode in which the upper portion and the lower portion of a purification column are reversed because of a specific gravity of the crystal relative to the mother liquid.

By the vertical melt purification column 70, purification can be carried out by countercurrent contact of the crystal moving to the lower portion with the liquid rising as a reflux liquid. In this case, the mixed mother liquid of the reflux liquid that has reached the clarified liquid discharge means in the upper portion and the mother liquid are discharged to be sent back to the crystallizer 20 in the previous stage, thereby making it possible to crystallize the target component and enhance the recovery rate of the crystal.

On the other hand, the evaporated vapor in the crystallizer 20 is allowed to pass a piping path 63, pressurized to a pressure higher than the operation pressure in the crystallizer 20 by the compressor 30, and then introduced to the absorption condenser 10. While bringing the mixture solution of organic compound (mixture solution 1) into contact with the evaporated vapor that has been pressurized in the absorption condenser 10, absorption and condensation are carried out by cooling with cooling heat that a cooling medium 2 (for example, cooling water in cooling column or brine in freezer) has, and this absorption condensate is introduced to the crystallizer 20.

When adiabatic cooling and evaporation operation for the liquid coolant component are carried out, in the crystallizer 20, for the mixture solution of the target organic compound containing the liquid coolant component, crystallization heat is taken away in association with the evaporation of the liquid coolant component, and crystal is crystallized.

The reason why the evaporated vapor is pressurized to a pressure higher than the operation pressure in the crystallizer 20 by the compressor 30 before being introduced to the absorption condenser 10 is that a temperature difference between the crystallizer 20 and the absorption condenser 10 is secured by means of pressurization by the compressor 30 in order to recondense the coolant at a temperature much higher than the operation temperature of the crystallizer 20.

In the absorption condenser 10, the evaporated vapor is brought into contact with the solution of the organic compound having high boiling points, and therefore the boiling point rises, thereby raising the temperature at which absorption and condensation can take place. Accordingly, a smaller energy input from outside suffices the need for absorption and condensation. It is possible to carry out continuous crystallization operation by introducing the absorption condensate in the absorption condenser 10 to the crystallizer 20.

Taking crystallization of p-xylene as an example, propane is used as a coolant, the pressure in the crystallizer 20 is, for example, normal atmospheric pressure, and the pressure in the absorption condenser 10 is, for example, about eight atmospheric pressure by means of pressurization by the compressor 30.

According to the operation, crystallization operation is possible without constructing the crystallizer 20 as a pressure resistant container. When at least the crystallizer 20, the compressor 30, and the absorption condenser 10 are included as necessary apparatuses, crystallization operation can be carried out, and therefore, an expensive structure installed with a refrigeration system that was used in the prior art is not necessary, thus giving rise to an economical apparatus in view of entire system cost and running cost.

The clarified liquid (mother liquid Mo) in the clarified portion in the crystallizer 20 can be discharged to the outside of the system through a piping path 64.

<Second Embodiment>

In a second embodiment shown in FIG. 3, not only is the clarified liquid (mother liquid Mo) in the upper clarified portion in the crystallizer 20 discharged to the outside of the system but also part of the clarified liquid is sent back, via a piping path 65, to the absorption condenser 10. By sending back the clarified liquid to the absorption condenser 10 as the mother liquid, condensation of the coolant vapor can be carried out at a further lower pressure. In this case, absorption and condensation can be carried out in a condition of a lowered concentration of the coolant by allowing the vapor to combine with the mixture solution of organic compound (mixture solution 1) and subsequently being supplied to the absorption condenser 10.

<Third Embodiment>

FIG. 4 represents a third embodiment. After the crystal slurry taken out of the crystallizer 20 is concentrated by a concentration means 40, the concentrated component is introduced to the purification means.

For the concentration, a centrifuge or a filter can also be used; however, a cyclone that is economically advantageous is adopted in the example in FIG. 4.

Since the coolant is contained in the liquid Mo discharged to the outside of the system by the concentration means 40 in a state where the coolant is dissolved in the discharged liquid Mo, the coolant can be recovered by a distillation column in the subsequent stage or the like, and further supplied as makeup to a suction means of the compressor 30 as a coolant gas 1A.

On the other hand, the clarified liquid separated in the melt purification column 70 can be sent back to the absorption condenser 10 via a piping path 66.

<Fourth Embodiment>

Figure 5:
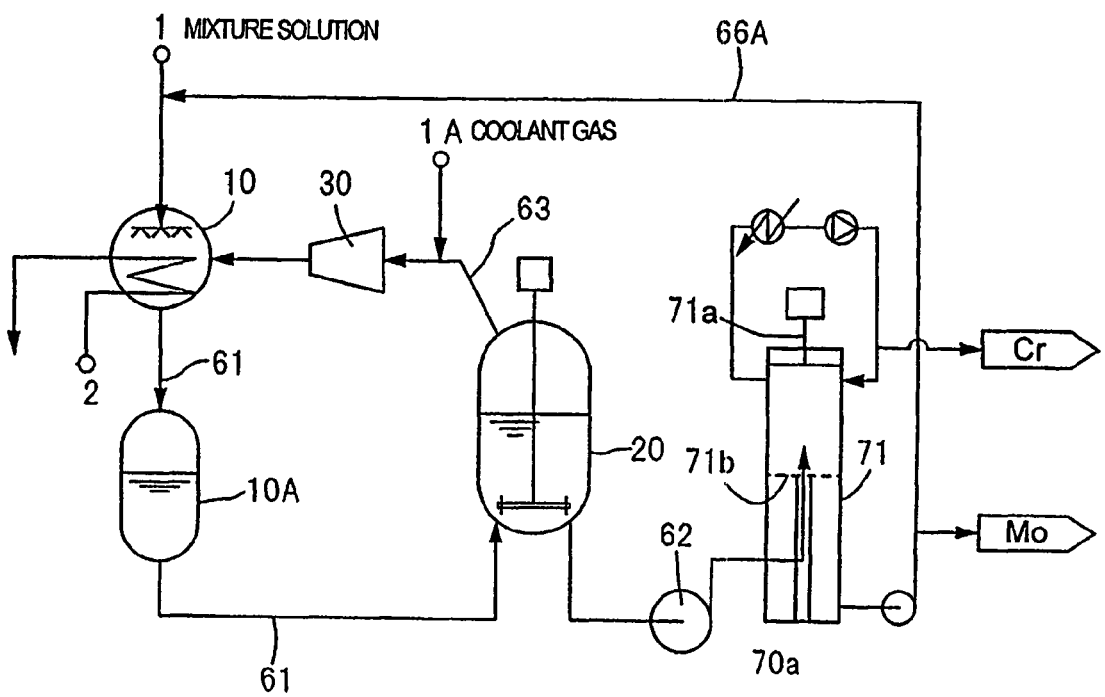
FIG. 5 is a flow sheet of a fourth embodiment.

With respect to the vertical melt purification column 70, purification can by carried out by an vertical melt purification column 71 of a structure in which the upper portion and the lower portion are reversed. In other words, as shown in FIG. 5, a clarified liquid discharge means is arranged in the lower portion, a heating means (not shown) is arranged in the upper portion, the crystal slurry taken out of the crystallizer 20 is introduced to the vertical melt purification column 71 having a mechanical means to form mechanically a crystal-filling layer inside, for example, a structure provided with a crystal bed scraper 71a and a filter 71b that reciprocates like a piston, and in the purification column 71, the crystal moving to the upper portion is molten by the heating means arranged in the upper portion, part of the molten matter is taken out for making a product, the other portion is allowed to fall as a reflux liquid, the rising crystal is washed of the mother liquid with this reflux liquid in the crystal-filling layer, the purified crystal is compacted by the mechanical means in the upper portion, and the mixed mother liquid of the reflux liquid that has reached the discharge means of mother liquid in the lower portion and the mother liquid is discharged to be sent back to the absorption condenser 10 via, for example, a piping path 66A. It is, of course, possible to send the mixed mother liquid to the crystallizer 20. A condenser and a compressor are provided to attach to the upper portion of the purification column 71.

<Explanation of a Method for Crystallization>

Taking a benzene-cyclohexane system as an example, the method for crystallization is explained.

In common production in chemical industry, cyclohexane is produced by hydrogenation of benzene.

$$C_6H_6 + 3H_2 \rightarrow C_6H_{12}$$

In this hydrogenation reaction, the following impurities are produced by side reactions.

methylcyclopentane
n-hexane
n-pentane
methylcyclohexane

In addition to these, toluene, and paraffins contained in the raw material benzene are included.

In such a case, what is the most difficult in obtaining cyclohexane with high purity is that it becomes almost impossible to separate cyclohexane by distillation when unreacted benzene is contained. The boiling point of benzene at normal atmospheric pressure is 80.75 degrees C., and that of cyclohexane is 80.16 degrees C. The difference between them is only 0.59 degree C. Further, the lowest azeotropic point (77.62 degrees C.) is around 54 mol % of cyclohexane.

Figure 1:
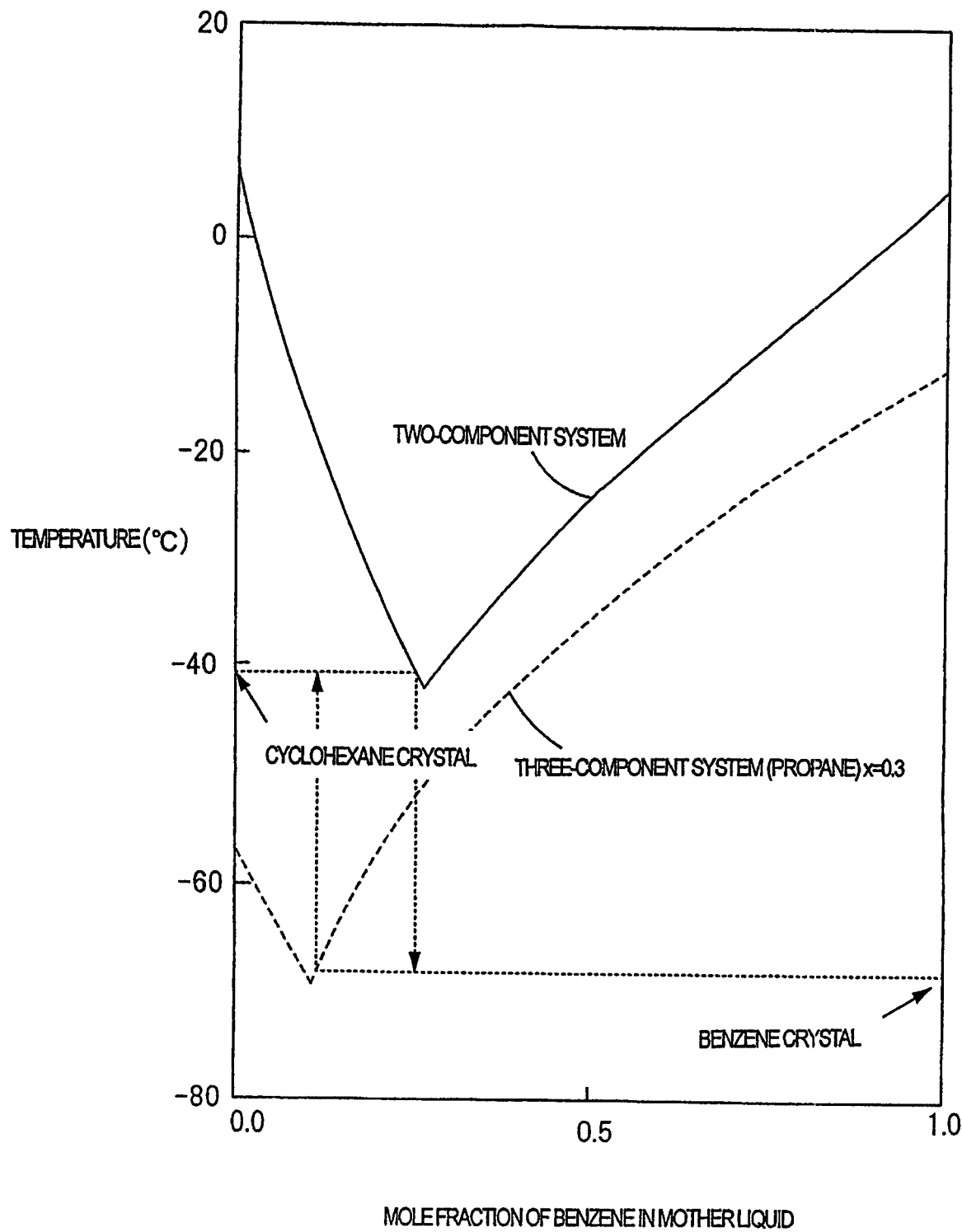
FIG. 1 is a solid-liquid equilibrium diagram of a eutectic composition of propane-benzene-cyclohexane system.

On the other hand, as is clear from the solid- liquid equilibrium diagram of a eutectic composition of propane-benzene-cyclohexane system shown in FIG. 1, a method of separation and purification by crystallization can be adopted when cyclohexane with high purity is desired to be obtained. In this method, it becomes possible to remove impurities such as methylcyclopentane contained together in a small amount at the same time.

In other words, in the phase diagram, a solid- liquid equilibrium line of the two-component system consisting of cyclohexane and benzene can be obtained. The content of impurities in a very small amount only slightly lowers the crystallization point curve, and there is no large substantial difference. When it is intended here that a mixed raw material rich in cyclohexane is cooled to crystallize cyclohexane, crystallization starts when the temperature reaches the solid-liquid line on the left side. Next, in the method for adiabatic cooling using propane, when a supply liquid and propane are mixed and cooling is started by releasing the pressure, crossing the solid-liquid equilibrium line (the line is drawn as component without propane) of the three-component system having added propane takes place. When cooling the liquid along the line to near the eutectic point, crystal of cyclohexane is crystallized, and this crystal is separated from the mother liquid.

Such operation is continuously carried out in the facility structured according to the present invention.

The mother liquid separated from the cyclohexane crystal is subjected to propane removal, mixed with the raw material, and fed back. Note that a mixed liquid system of benzene and cyclohexane is a eutectic system in the range of all concentrations. The crystallization point of pure benzene is 5.5 degrees C. and that of cyclohexane is 5.7 degrees C.

From the explanation of this principle, it will be obvious that cyclohexane crystal can be obtained from a eutectic composition of propane-benzene-cyclohexane system. Further, according to the present invention, it will be also clear that a low cost crystallization process is provided for their separation.

<Other Explanations>

The above embodiments are examples in which one crystallizer is used. However, the present invention also aims at a structure provided with a plurality of crystallizers. In a facility provided with a plurality of crystallizers, crystal slurry in a crystallizer in a previous stage is introduced to a crystallizer in the subsequent stage, followed by carrying out further crystallization. And a crystallizer in the final stage is combined with the purification means.

In this mode, when the clarified liquid in the purification means is sent back to a crystallizer, it is desirable to send it back to the crystallizer in the final stage, and when it is sent back to the absorption condenser, it is desirable to introduce it to the absorption condenser attached to the initial stage.

When the coolant is a gas component, the solvent-agent dissolved in the mother liquid is removed as a gas by contacting the molten liquid refluxed from the lower portion as a countercurrent washing liquid in the purification column, showing a stripping effect, and therefore it is possible to obtain a high purification effect compared with a case in which crystal is separated from the crystal slurry by simple solid-liquid separation.

Further, in the present invention, a purification column to form a crystal bed by a mechanically driven power can also be used, as in the example of FIG. 5, in place of the gravity precipitation type purification columns shown in FIGS. 2 to 4. In this case, the concentration means in the above embodiment becomes unnecessary, and the crystal mother liquid can be discharged to the outside of the system as it is.

The mechanically driven type purification column can employ any one of the types in which a crystal bed is formed in the upper portion of the column and a crystal bed is formed in the lower portion thereof. However, there is a possibility that generated gas may cause a failure in formation of crystal bed and reduction in product purity. Therefore, the use of the type in which a bed is formed in the lower portion is preferred.

EXAMPLE

Hereinafter, the effects of the present invention are made clear by showing an example.

Example 1

In the following example, crystallization was carried out by the process shown in FIG. 4. An vertical crystallizer (300 millimeter diameter×1.5 meter height, slurry hold-up capacity of 25 liters) was used as the crystallizer 20, and a horizontal tube type absorption condenser was used for the absorption condenser 10.

A raw material of xylene mixture having 80 to 90% paraxylene concentration at normal temperature was supplied to the absorption condenser 10 at a rate of 15 to 25 kg/hr and condensed at about 30 degrees C. while being brought into contact with and mixed with the vapor pressurized to 0.2 to 0.7 megapascal (MPa) by passing through the compressor 30 from the crystallizer 20. The obtained condensed liquid was a solution of xylene mixture containing propane at a concentration of 10 to 30%. This solution was introduced to the crystallizer 20 being run at −10 to 0 degree C. under normal atmospheric pressure for crystallization. The paraxylene crystal slurry obtained by the crystallization was supplied to the purification column 70 from the crystallizer 20 via a liquid cyclone 40. As the result, purified paraxylene solution having a purity of equal to or more than 98 to 99.9% by wt. could be obtained at 4 to 7 kg/hr. The clarified liquid from the cyclone that was the solution of xylene mixture with propane was discharged to the outside of the system. The propane in the portion discharged to the outside of the system in a state that the propane was dissolved in the clarified liquid was supplied to the suction means of the compressor 30 as make-up. The concentration of paraxylene in the clarified liquid was 60 to 80%. The overflow from the purification column 70 containing a high proportion of paraxylene was sent back to the absorption condenser 10 as a liquid for reabsorption.

What is claimed is:

1. A method for adiabatic cooling type crystallization of organic compound comprising: introducing a mixture solution containing a target organic compound along with coolant condensate into a crystallizer, and performing evaporation operation to the coolant within the crystallizer so as to execute adiabatic cooling by the evaporation operation, thus carrying out crystallization operation of the target organic compound;

taking out organic compound crystal slurry, which is produced by the crystallization operation, from the crystallizer;

pressurizing the evaporated coolant vapor, which is obtained from the evaporation operation of the coolant vapor, to a pressure higher than operation pressure in the crystallizer by a compressor and then introducing the pressurized evaporated coolant vapor to an absorption condenser;

cooling, by a cooling column through which cooling water passes, the pressurized evaporated coolant vapor and the mixture solution, while allowing the pressurized evaporated coolant vapor and the mixture solution to contact each other, thus allowing the mixture solution to be subjected to absorption and condensation of the pressurized coolant vapor; and introducing the crystal slurry taken out of the crystallizer to a purification means to purify the crystal, and introducing a clarified liquid in the purification means to at least one of the crystallizer and the absorption condenser as it is, and wherein the purification means is an vertical melt purification column having a clarified liquid discharge means in the lower portion and a heating means in the upper portion, to-the crystal slurry taken out of the crystallizer being introduced into the purification means, and in the purification column, the crystal moving to the upper portion is molten by the heating means in the upper portion, part of the molten matter or the molten liquid containing the crystal is taken out for making a product, the other portion is allowed to fall, as a reflux liquid, through a crystal group that is rising, the mother liquid is washed out with the reflux liquid, the purified crystal is allowed to move upward, and the clarified liquid having reached the clarified liquid discharge means in the lower portion is introduced to the absorption condenser as it is.

2. The method for adiabatic cooling type crystallization of organic compound according to claim 1, wherein the crystal slurry taken out of the crystallizer is introduced to the purification means after being concentrated by a concentration means.

3. The method for adiabatic cooling type crystallization of organic compound according to claim 1, wherein the clarified liquid in a clarified portion in the crystallizer is introduced to the absorption condenser.

4. The method for adiabatic cooling type crystallization of organic compound according to claim 1, wherein the operation pressure in the crystallizer is around normal atmospheric pressure or equal to or lower than four atmospheric pressure, and the evaporated coolant vapor, which is obtained from the evaporation operation of the coolant vapor, is pressurized to a pressure which is higher than operation pressure in the crystallizer and equal to or lower than eight atmospheric pressure.

5. The method for adiabatic cooling type crystallization of organic compound according to claim 1, wherein the concentration of the coolant in the absorption condensate from the absorption condenser is set to from 1 to 70%.

6. The method for adiabatic cooling type crystallization of organic compound according to claim 1, wherein the mixture solution of organic compound is a xylene mixture containing paraxylene and the coolant vapor is propane.

7. The method for adiabatic cooling type crystallization of organic compound according to claim 2, wherein the coolant dissolved in a discharged liquid discharged by the concentration means to outside of a system is recovered and supplied as make-up to a suction means of the compressor.

* * * * *